(12) United States Patent
Swartz et al.

(10) Patent No.: US 6,548,276 B2
(45) Date of Patent: Apr. 15, 2003

(54) ENHANCED IN VITRO SYNTHESIS OF ACTIVE PROTEINS CONTAINING DISULFIDE BONDS

(75) Inventors: James Robert Swartz, Menlo Park, CA (US); Dong-Myung Kim, Walnut Creek, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/948,052

(22) Filed: Sep. 5, 2001

(65) Prior Publication Data

US 2002/0058303 A1 May 16, 2002

Related U.S. Application Data

(60) Provisional application No. 60/230,381, filed on Sep. 6, 2000.

(51) Int. Cl.[7] ............................. C12P 21/00; C12Q 1/02; A61K 38/00; C07K 1/00
(52) U.S. Cl. ....................... 435/70.1; 435/68.1; 435/25; 435/7.9; 435/189; 435/215; 435/320.1; 530/350; 514/12; 536/23.1
(58) Field of Search ............................... 435/70.1, 68.1, 435/215, 189, 7.9, 25, 320.1; 530/350; 514/12; 536/23.1

(56) References Cited

PUBLICATIONS

Ryabova, Lyubov A., *Functional antibody production using cell–free translation: Effects of protein disulfide isomerase and chaperones*, Nature Biotechnology, Jan. 1997, vol. 15.
Bukau, B. et al., *The Hsp70 and Hsp60 Chaperone Machines*, Review, Cell, A Scientific Breakthrough, vol. 92, 351–366, Cell Press (Feb. 1998).

Bessette, P.H. et al., *Efficient folding of proteins with multiple disulfide bonds in the Escherichia coli cytoplasm*, PNAS, vol. 96, No. 24, 13703–13708 (Nov. 23, 1999).
Kim, D.M. et al., *Prolonging Cell–Free Protein Synthesis by Selective Reagent Additions*, Biotechnol Prog. May–Jun. 2000; 16(3):385–90 (2000).
Kim, D.M. et al., *Prolonging Cell–Free Protein Synthesis with a Novel ATP Regeneration System*, Biotechnology and Bioengineering, vol. 66, No. 3, pp. 180–188 (1999).
Kim, D.M. et al., *A highly efficient cell–free protein synthesis system foo Escherichia coli*, Eur. J. Biochem. 239, pp. 881–886, FEBS (1996).
Missiakas, D. et al., *Protein Folding in the Bacterial Periplasm*, Minireview, Journal of Bacteriology, vol. 179, No. 8, p. 2465–2471, American Society for Microbiology (Apr. 1997).
Noren, C.J. et al., *A General Method for Site–Specific Incorporation of Unnatural Amino Acids into Proteins*, Science, Research Articles, vol. 244, pp. 182–188 (Apr. 14, 1989).
Richardson, A., et al., *The ins and outs of a molecular chaperone machine*, Reviews, TIBS, pp. 138–143, Elsevier Science Ltd. (Apr. 23, 1998).
Qiu, J. et al., *Expression of Active Human Tissue–Type Plasminogen Activator in Escherichia coli*, Applied and Environmental Microbiology, vol. 64, No. 12, pp. 4891–4896, 0099–2240, American Society for Microbiology (Dec. 1998).

*Primary Examiner*—Gabrielle Bugaisky
*Assistant Examiner*—Chih-Min Kam
(74) *Attorney, Agent, or Firm*—Pamela J. Sherwood; Bozicevic, Field & Francis LLP

(57) ABSTRACT

Compositions and methods are provided for the enhanced in vitro synthesis of polypeptides containing disulfide bonds. In order to improve the performance of in vitro protein synthesis reactions, pre-treatment and redox buffering of the reaction mix is performed in order to optimize the redox potential. Exogenous enzymes that enhance protein folding and disulfide bond formation may also be added to the reaction.

12 Claims, 8 Drawing Sheets

ENHANCED IN VITRO SYNTHESIS OF ACTIVE PROTEINS CONTAINING DISULFIDE BONDS

CROSS REFERENCE

This application claims benefit of United States Provisional Application Serial No. 60/230,381 filed Sept. 6, 2000.

BACKGROUND OF THE INVENTION

*Escherichia coli* is a widely used organism for the expression of heterologous proteins. It easily grows to a high cell density on inexpensive substrates to provide excellent volumetric and economic productivities. Well established genetic techniques and various expression vectors further justify the use of Escherichia coli as a production host. However, a high rate of protein synthesis is necessary, but by no means sufficient, for the efficient production of active biomolecules. In order to be biologically active, the polypeptide chain has to fold into the correct native three-dimensional structure, including the appropriate formation of disulfide bonds.

In many cases, the recombinant polypeptides have been found to be sequestered within large refractile aggregates known as inclusion bodies. Active proteins can be recovered from inclusion bodies through a cycle of denaturant-induced solubilization of the aggregates followed by removal of the denaturant under conditions that favor refolding. But although the formation of inclusion bodies can sometimes ease the purification of expressed proteins; in most occasions, refolding of the aggregated proteins remains a challenge.

Various attempts have been made to improve the folding of heterologous proteins in the bacterial cytoplasm. In addition to the traditional methods, including lowering the temperature of the culture, increasing knowledge of the mechanism and effectors of protein folding has enabled new approaches to solve the problem of aggregation.

Studies in vitro have demonstrated that, for the vast majority of polypeptides, folding is a spontaneous process directed by the amino acid sequence and the solvent conditions. Yet, even though the native state is thermodynamically favored, the time-scale for folding can vary from milliseconds to days. Kinetic barriers are introduced, for example, by the need for alignment of subunits and sub-domains. And particularly with eukaryotic proteins, covalent reactions must take place for the correctly folded protein to form. The latter types of reaction include disulfide bond formation. cis/trans isomerization of the polypeptide chain around proline peptide bonds, preprotein processing and the ligation of prosthetic groups. These kinetic limitations result in the accumulation of partially folded intermediates, that contain exposed hydrophobic 'sticky' surfaces which promote self-association and formation of aggregates.

Expression of mammalian proteins is more complicated than bacterial proteins because most of them require intramolecular disulfide bonds for their activity. Thus additional effectors such as foldases and proper redox potential are required to achieve their native structures. Even though the periplasmic space of Escherichia coli provides an oxidizing environment as well as folding proteins such as DsbA, B, C, and D; in many cases, simple secretion of complex proteins into the periplasmic space is not sufficient to form correct disulfide bonds.

Accessory proteins known as foldases and chaperones have been found to assist in the proper folding of proteins in vivo. Foldases have a catalytic activity that serves to accelerate rate-limiting covalent steps in folding. Chaperones, on the other hand, perform many functions, the most important of which is to provide an environment for nascent proteins to fold without the competing process of self-association. In addition to the well-characterized molecular chaperones, such as GroEL and DnaK proteins, a number of additional cytoplasmic proteins have been identified to affect the folding of heterologous proteins.

Following the discovery of numerous bacterial or eukaryotic foldases and their specific roles in the oxidation and isomerization of disulfide bonds, many attempts have been made to use those proteins in the periplasmnic space or even in the cytoplasm of *Escherichia coli* (see, for example, Bessette et al. (1999)). The co-expression of molecular chaperones has been shown to partially solve the problem of inclusion body formation in the expression of certain recombinant proteins (see, for example, Richardson et al. (1998) *Trends Biochem. Sci.* 23:138–143; and Bukau et al. (1998) *Cell* 92:351–366).

However, the effect of molecular chaperones is rather product-specific and the co-expression of each molecular chaperone with the target proteins is often cumbersome. Moreover, in some cases, the expression of a molecular chaperone is harmful or even detrimental to cell growth. Despite the recent advances, the expression of properly folded mammalian proteins in *Escherichia coli* still remains as a great challenge. This is mainly due to the difficulties in the control of the key parameters for disulfide bond formation including the redox potential inside the cells.

For several decades, in vitro protein synthesis has served as an effective tool for lab-scale expression of cloned or synthesized genetic materials. In recent years, in vitro protein synthesis has been considered as an alternative to conventional recombinant DNA technology, because of disadvantages associated with cellular expression. In vivo, proteins can be degraded or modified by several enzymes synthesized with the growth of the cell, and, after synthesis, may be modified by post-translational processing, such as glycosylation, deamidation or oxidation. In addition, many products inhibit metabolic processes and their synthesis must compete with other cellular processes required to reproduce the cell and to protect its genetic information.

Because it is essentially free from cellular regulation of gene expression, in vitro protein synthesis has advantages in the production of cytotoxic, unstable, or insoluble proteins. The over-production of protein beyond a predetermined concentration can be difficult to obtain in vivo, because the expression levels are regulated by the concentration of product. The concentration of protein accumulated in the cell generally affects the viability of the cell, so that overproduction of the desired protein is difficult to obtain. In an isolation and purification process, many kinds of protein are insoluble or unstable, and are either degraded by intracellular proteases or aggregate in inclusion bodies, so that the loss rate is high.

In vitro synthesis circumvents many of these problems (see Kim and Swartz (1999) *Biotechnol. Bioeng.* 66:180–188; and Kim and Swartz (2000) *Biotechnol. Prog.* 16:385–390). Also, through simultaneous and rapid expression of various proteins in a multiplexed configuration, this technology can provide a valuable tool for development of combinatorial arrays for research, and for screening of proteins. In addition, various kinds of unnatural amino acids can be efficiently incorporated into proteins for specific purposes (Noren et al. (1989) *Science* 244:182–188).

Unlike in vivo gene expression, cell-free protein synthesis uses isolated translational machinery instead of entire cells. As a result, this method eliminates the requirement to maintain cell physiology and allows direct control of various parameters to optimize the synthesis/folding of target proteins. Of particular interest is the problem of cell-free synthesis of biologically active mammalian proteins having multiple disulfide bonds. The present invention addresses the coupled synthesis and folding of mammalian proteins through the control of redox potential during protein synthesis.

SUMMARY OF THE INVENTION

Compositions and methods are provided for the enhanced in vitro synthesis of protein molecules, by optimizing the redox conditions in the reaction mix. In one embodiment of the invention, a redox buffer is included in the reaction mix to maintain the appropriate oxidizing environment for the formation of proper disulfide bonds, for example by the inclusion of glutathione in an appropriate ratio of oxidized to reduced forms.

The reaction mix is preferably further modified to decrease the activity of molecules in the extract, e.g. endogenous enzymes that have reducing activity. Preferably such molecules are chemically inactivated prior to cell-free protein synthesis, e.g. by treatment of the extracts with iodoacetamide (IAA), or other compounds that irreversibly inactivate free sulfhydryl groups. The presence of endogenous enzymes having reducing activity may be further diminished by the use of extracts prepared from genetically modified cells having inactivating mutations in such enzymes, for example thioredoxin reductase, glutathione reductase, etc.

In addition to stabilizing the redox potential of the reaction mix, the in vitro synthesis may be further enhanced by the inclusion of accessory proteins that assist in the proper folding of proteins in vivo. Of particular interest is the inclusion of foldases, proteins with a catalytic activity that serve to accelerate rate-limiting covalent steps in folding, e.g. PDI, dsbC, etc.

DETAILED DESCRIPTION OF THE EMBODIMENTS

Figure 1:
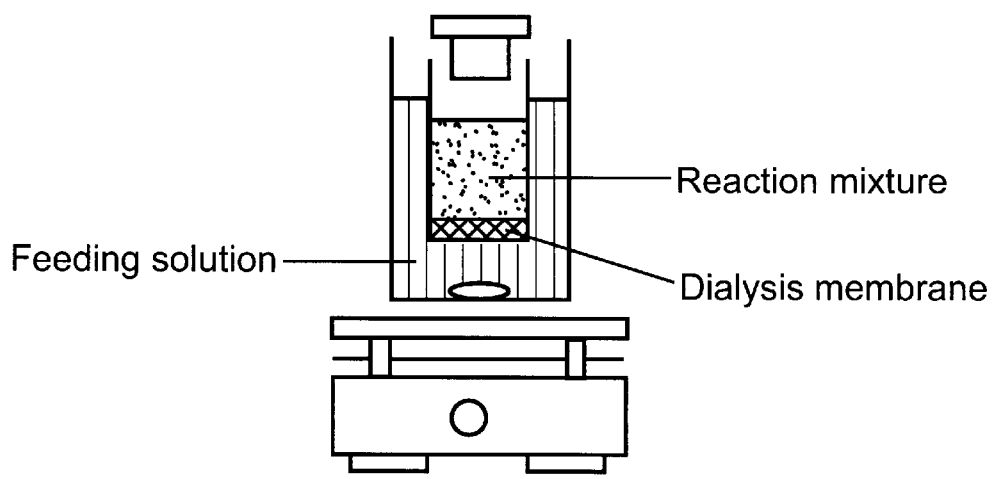
FIG. 1 shows the reactor used for the semicontiunous reactions.

Compositions and methods are provided for the enhanced in vitro synthesis of biologically active proteins, particularly proteins comprising one or more disulfide bonds. The reaction mix for in vitro protein synthesis is modified to improve protein folding, and formation of disulfide bonds. A redox buffer is included in the reaction mix to maintain the appropriate oxidizing environment, for example by the inclusion of glutathione in an appropriate ratio of oxidized to reduced forms. That redox buffer is further stabilized by inactivating endogenous oxidoreductase reactions. The inclusion of a redox buffer enables the production of bioactive proteins that require the formation of one or more intramolecular disulfide bonds for activity.

In a preferred embodiment, endogenous molecules that reduce the redox buffer are chemically inactivated prior to synthesis, e.g. by treatment of the extracts with compounds such as iodoacetamide (IAA), which irreversibly inactivate free sulfhydryl groups.

In some methods of in vitro protein synthesis, endogenous enzymes are utilized for the generation or replenishment of energy sources used in the reaction (see, for example, co-pending patent application Ser. No. 09/270,814). In some instances, such endogenous enzymes are inactivated by the chemical inactivation step described above, and in that case it may be desirable to replenish these enzymes from an exogenous source, prior to, or concurrent with synthesis. By way of example, if the use of non-traditional secondary energy sources such as early glycolytic intermediates (for example, glucose 6-phosphate) is desired, the activity of glyceraldehyde 3-phosphate dehydrogenase can be restored by any of several methods known in the art.

The presence of endogenous enzymes having reducing activity may be further diminished by the use of extracts prepared from genetically modified cells having inactivating mutations in such enzymes, for example thioredoxin reductase, glutathione reductase, etc.

In addition to buffering the redox potential of the reaction mix, the in vitro synthesis may be further enhanced by the inclusion of accessory proteins that assist in the proper folding of proteins in vivo. Of particular interest is the inclusion of foldases, proteins with a catalytic activity that serve to accelerate rate-limiting covalent steps in folding, e.g. PDI, dsbC, etc.

These methods are applicable to continuous, semi-continuous and batch reactions. In the semi-continuous system, even where the endogenous reducing enzymes are not inactivated, the level of oxidation of the redox buffer will recover substantially after an extended incubation. The recovery of an oxidizing environment in the reaction chamber allows the synthesized protein to acquire disulfide bonds and activity. However, the extracts with inactivated oxidoreductases provide more rapid formation of bioactive proteins.

For some synthetic reactions, e.g. multiplexed reactions, it is preferable to use batch rather than a semi-continuous system. For batch synthesis methods, the reaction mix is preferably modified to decrease the activity of molecules in the extract, e.g. endogenous enzymes, that have reducing activity.

Definitions

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Folding, as used herein, refers to the three-dimensional structure of polypeptides and proteins, where interactions between amino acid residues act to stabilize the structure. While non-covalent interactions are important in determining structure, usually the peptides and proteins of interest will have intra- and/or intermolecular covalent bonds formed by two cysteine residues. For naturally occurring proteins and polypeptides or derivatives and variants thereof, the proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

In vitro synthesis: as used herein refers to the cell-free synthesis of polypeptides in a reaction mix comprising biological extracts and/or defined reagents. The reaction mix will comprise at least ATP, an energy source; a template for production of the macromolecule, e.g. DNA, mRNA, etc.; amino acids, and such co-factors, enzymes and other reagents that are necessary for the synthesis, e.g. ribosomes, tRNA, polymerases, transcriptional factors, etc. Such synthetic reaction systems are well-known in the art, and have been described in the literature. The cell free synthesis reaction may be performed as batch, continuous flow, or semi-continuous flow, as known in the art.

Redox buffer. The synthetic reaction mix in the present invention is modified by the addition of a redox buffer. Such a buffer comprises compounds with free sulfhydryl groups, such as one or more of glutathione, dithiothreitol, dithioerythritol, βmercaptoethanol, thioglycolate, cysteine, etc. The concentration of reducing agent and the ratio of the oxidized and reduced forms necessary to achieve the reducing power desired for the selected reaction time will vary according to the strength of the reducing agent, the level of $O_2$ in the system, and the length of the reaction time.

In a preferred embodiment, glutathione is used as the redox buffering agent, and is added at a concentration of at least about 1 mM and not more than about 25 mM, preferably at a concentration of about 5 to 10 mM.

The redox buffer may comprise both the oxidized and reduced forms of the sulfhydryl compound, for example in a ratio of between about 10:1 to 1:1 of oxidized:reduced forms, usually in a ratio between about 5:1 to 2:1, and may be in a ratio of 4:1.

Biological extracts. For the purposes of this invention, biological extracts are any preparation comprising the components of a protein synthesis machinery, usually a bacterial cell extract, wherein such components are capable of expressing a nucleic acid encoding a desired protein. Thus, a bacterial extract comprises components that are capable of translating messenger ribonucleic acid (mRNA) encoding a desired protein, and optionally comprises components that are capable of transcribing DNA encoding a desired protein. Such components include, for example, DNA-directed RNA polymerase (RNA polymerase), any transcription activators that are required for initiation of transcription of DNA encoding the desired protein, transfer ribonucleic acids (tRNAs), aminoacyl-tRNA synthetases, 70S ribosomes, $N^{10}$-formyltetrahydrofolate, formylmethionine-tRNA$f^{Met}$ synthetase, peptidyl transferase, initiation factors such as IF-1, IF-2 and IF-3, elongation factors such as EF-Tu, EF-Ts, and EF-G, release factors such as RF-1, RF-2, and RF-3, and the like.

In a preferred embodiment of the invention, the reaction mixture comprises extracts from bacterial cells, e.g. *E. coli* S30 extracts, as is known in the art. For convenience, the organism used as a source of extracts may be referred to as the source organism. Methods for producing active extracts are known in the art, for example they may be found in Pratt (1984), Coupled transcription-translation in prokaryotic cell-free systems, p. 179–209, in Hames, B. D. and Higgins, S. J. (ed.), Transcription and Translation: A Practical Approach, IRL Press, New York. Kudlicki et al. (1992) *Anal Biochem* 206(2):389–93 modify the S30 *E. coli* cell-free extract by collecting the ribosome fraction from the S30 by ultracentrifugation. While such extracts are a useful source of ribosomes and other factors necessary for protein synthesis, they can also contain small amounts of enzymes responsible for undesirable side-reactions that are unrelated to protein synthesis, but which modulate the oxidizing environment of the reaction, and which can act to reduce the groups on the nascent polypeptide and the redox buffer.

Redox optimized extracts. The biological extracts for the present methods are preferably optimized to substantially eliminate enzymes and other biomolecules present in the extract that act to reduce the redox buffer. The undesirable enzymes, may be removed or otherwise inactivated in the reaction mix.

In a preferred embodiment, the endogenous molecules having free sulfhydryl groups are inactivated prior to the initiation of synthesis by treatment with a compound that chemically blocks the sulfhydryl, e.g. by alkylation or acetylation of the free sulfhydryl. The inactivating compound is then removed from the reaction mix, e.g. by dialysis, etc.

Useful inactivating agents include iodoacetamide, N-ethyl maleimide, iodoacetate, N-iodoacetyl-N'-(5-sulfonic-1-naphthyl) ethylene diamine, etc., as known in the art; especially those compounds including iodoacetamides, maleimides, benzylic halides and bromomethylketones. The concentration of inactivation agent and length of time for the reaction will be determined by the specific compound that is chosen. The inactivation agent is added at a concentration that substantially eliminates the endogenous sulfhydryl reducing activity, while maintaining the synthetic activity of the extract. Both activities are readily determined by methods illustrated in the listed examples. Usually at least about 50% of the synthetic activity will be retained, more usually at least about 75%, and preferably at least about 90%. As an example, where the inactivation agent is iodoacetamide, it may be added at a concentration of from about 1 to 10 mM, and incubated from between 15 to 60 minutes.

In addition to the use of an inactivation agent to pre-treat the biological extracts, the reducing activity of the extract may be further modified by the genetic modification of the source strain to "knock-out", or genetically inactivate enzymes having this undesirable activity. Such enzymes may include thioredoxin reductase, glutathione reductase, and the like.

The coding sequence for the enzyme is "knocked-out" or otherwise inactivated in the chromosome of the source organism, by deletion of all or a part of the coding sequence; frame-shift insertion; dominant negative mutations, etc. The genomes of a number of organisms, including *E. coli,* have been completely sequenced, thereby facilitating the genetic modifications. For example, a markerless knockout strategy method is described by Arigoni et al. (1998) *Nat Biotechnol* 16(9):851–6.

A preferred method for inactivating targeted genes is described by Hoang et al. (1998) *Gene* 212:77–86. In this method, gene replacement vectors are employed that contain a tetracycline resistance gene and a gene encoding levan sucrase (sacB) as selection markers for recombination. The target gene is first cloned and mutagenized, preferably by deleting a significant portion of the gene. This gene is then inserted by ligation into a vector designed for facilitating chromosomal gene replacement. The *E. coli* cells are then transformed with those vectors. Cells that have incorporated the plasmid into the chromosome at the site of the target gene are selected, then the plasmid is forced to leave the chromosome by growing the cells on sucrose. Sucrose is toxic when the sacB gene resides in the chromosome. The properly mutated strain is selected based on its phenotype of tetracycline sensitivity and sucrose resistance. PCR analysis or DNA sequencing then confirms the desired genetic change.

The enzyme can be removed from the cell extract after cell disruption and before use. Any of the several means known in the art of protein purification may be used, including affinity purification techniques such as the use of antibodies or antibody fragments with specific affinity for the target enzymes; use of affinity tags expressed as part of the target enzymes to facilitate their removal from the cell extract; and conventional purification methods.

For example, an antibody or antibody fragment (e.g., Fab or scFv) is selected for specific affinity for the target enzyme using phage display or other well developed techniques. That antibody or antibody fragment is then immobilized on any of several purification beads or resins or membranes using any of several immobilization techniques. The immobilized antibody is contacted with the cell extract to bind to the target enzyme, and the immobilized antibody/enzyme complex then removed by filtration or gentle centrifugation.

In another example, the coding sequence of the targeted protein may be modified to include a tag, such as the Flag® extension (developed by Immunex Corp. and sold by Stratagene), or a poly-histidine tail. Many other examples have been published and are known to those skilled in the art. The tagged proteins are then removed by passage over the appropriate affinity matrix or column. The amino acid extension and binding partner are chosen so that only specific binding occurs under conditions compatible with the stability of the cell extract, and without significantly altering the chemical composition of the cell extract.

In yet another example, the target enzyme or enzymes are separated by any of several methods commonly used for protein purification, such as substrate affinity chromatography, ion exchange chromatography, hydrophobic interaction chromatography, electrophoretic separation, or other methods practiced in the art of protein purification.

Addition of folding enzymes. The reaction mixture of the present invention may be further modified by the inclusion of one or more enzymes that enhance folding and disulfide bond formation, i.e. foldases, chaperoning, etc. In one embodiment of the invention, a bacterial foldase enzyme is added to the reaction mix. A number of cysteine oxidoreductases catalyzing disulfide bond formation have been characterized in *E. coli,* for example. Enzymes or chaperonins of interest include DsbA, DsbC, PDI, GroEL, DnaK, DnaJ, GroEL/ES, GrpE, BIP, PPI or other cyclophilins, etc. The folding enzyme(s) are added at a concentration effective to improve the overall activity of the target protein of interest, which may be empirically determined by titrating the biological activity of the expressed protein product.

Of particular interest is the inclusion of DsbC, a soluble enzyme with oxidase and isomerase activity that catalyzes the rearrangement, or isomerization, of incorrect disulfide bonds. Incorrect pairing of cysteine residues occurs readily when an unfolded polypeptide chain is first oxidized. DsbC facilitates the disruption of incorrect disulfide bonds and the subsequent formation of those that occur in the native state. Also of interest is the use of the soluble enzyme DsbA, which is a main catalyst of disulfide bond formation.

Identification of the DsbC gene is described by Missiakas et al. (1994) *EMBO J* 13:2013–2020, where it is shown to have an activity similar to of DsbA in the dithiothreitol-dependent reduction of insulin in vitro. Also see Chen et al. (1999) *J. Biol. Chem.* 274:19601–19605. The use of DsbA or DsbC for enhancing periplasmic folding is discussed by Joly et al. (1998) *P.N.A.S.* 95:2773–2777.

As an alternative to bacterial enzymes, eukaryotic enzymes may be used. For example, the eukaryotic PDI is not only an efficient catalyst of protein cysteine oxidation and disulfide bond isomerization, but also exhibits chaperone activity. Co-expression of PDI can even facilitate the production of active proteins having multiple disulfide bonds. The reason why PDI is so effective in enhancing the folding of recombinant proteins in bacteria is presumably because it contains a peptide-binding subdomain that allows it to interact with heterologous proteins more readily than the bacterial enzymes. The inclusion of mammalian PDI provides an excellent catalyst of disulfide-bond isomerization in vitro.

The terms "desired protein" or "selected protein" are used interchangeably and refer generally to any peptide or protein having more than about 5 amino acids. The polypeptides may be homologous to, or preferably, may be exogenous, meaning that they are heterologous, i.e., foreign, to the bacteria from which the bacterial cell-free extract is derived, such as a human protein or a yeast protein produced in the bacterial cell-free extract. Preferably, mammalian polypeptides, i.e. polypeptides encoded in a mammalian genome are used.

Examples of mammalian polypeptides include, but are not limited to, molecules such as renin; growth hormones, including human growth hormone; bovine growth hormone; growth hormone releasing factor; parathyroid hormone; thyroid stimulating hormone; lipoproteins; alpha-1-antitrypsin; insulin A-chain; insulin; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES and other chemokines; human macrophage inflammatory protein (MIP-1α); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as αFGF and βFGF; epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1–3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-18; superoxide dismutase; T-cell receptors; surface membrane proteins; decay accelerating factor; viral antigen such as, for example, a portion of the AIDS envelope; transport proteins; homing receptors; addressing; regulatory proteins; antibodies; and fragments of any of the above-listed polypeptides.

Methods for Enhanced in Vitro Synthesis

The subject system is useful for in vitro protein synthesis of biologically active proteins, particularly proteins requiring correct formation of one or more disulfide bonds for biological activity. The synthesis reactions may include the transcription of RNA from DNA or RNA templates. The reactions may utilize a large scale reactor, small scale, or may be multiplexed to perform a plurality of simultaneous syntheses. Continuous reactions will use a feed mechanism to introduce a flow of reagents, and may isolate the end-product as part of the process. Batch systems are also of interest, where additional reagents may be introduced to prolong the period of time for active synthesis. A reactor may be run in any mode such as batch, extended batch, semibatch, semi-continuous, fed-batch and continuous, and which will be selected in accordance with the application purpose.

Of particular interest is the translation of mRNA to produce proteins, which translation may be coupled to in vitro synthesis of mRNA from a DNA template. Such a cell-free system will contain all factors required for the translation of mRNA, for example ribosomes, amino acids, tRNAs, aminoacyl synthetases, elongation factors and initiation factors. Cell-free systems known in the art include wheat germ extracts (Roberts et al. (1973) *P.N.A.S.* 70:2330), reticulocyte extracts (Pelham et al. (1976) *Eur. J. Biochem.* 67:247), *E. coli* extracts, etc., which can be treated with a suitable nuclease to eliminate active endogenous mRNA.

In addition to the above components such as cell-free extract, genetic template, amino acids and energy sources, materials specifically required for protein synthesis may be added to the reaction. These materials include salt, polymeric compounds, cyclic AMP, inhibitors for protein or nucleic acid degrading enzymes, inhibitor or regulator of protein synthesis, oxidation/reduction adjuster, non-denaturing surfactant, buffer component, spermine, spermidine, etc.

The salts preferably include potassium, magnesium, ammonium and manganese salt of acetic acid or sulfuric acid, and some of these may have amino acids as a counter anion. The polymeric compounds may be polyethylene glycol, dextran, diethyl aminoethyl, quaternary aminoethyl and aminoethyl. The oxidation/reduction adjuster may be dithiothreitol, ascorbic acid, glutathione and/or their oxides. Also, a non-denaturing surfactant such as Triton X-100 may be used at a concentration of 0–0.5 M. Spermine and spermidine may be used for improving protein synthetic ability, and cAMP may be used as a gene expression regulator.

When changing the concentration of a particular component of the reaction medium, that of another component may be changed accordingly. For example, the concentrations of several components such as nucleotides and energy source compounds may be simultaneously controlled in accordance with the change in those of other components. Also, the concentration levels of components in the reactor may be varied over time.

Preferably, the reaction is maintained in the range of pH 5–10 and a temperature of 20–50° C., and more preferably, in the range of pH 6–9 and a temperature of 25–40° C.

When using a protein isolating means in a continuous operation mode, the product output from the reactor flows through a membrane into the protein isolating means. In a semi-continuous operation mode, the outside or outer surface of the membrane is put into contact with predetermined solutions that are cyclically changed in a predetermined order. These solutions contain substrates such as amino acids and nucleotides. At this time, the reactor is operated in dialysis, diafiltration batch or fed-batch mode. A feed solution may be supplied to the reactor through the same membrane or a separate injection unit. Synthesized protein is accumulated in the reactor, and then is isolated and purified according to the usual method for protein purification after completion of the system operation.

Where there is a flow of reagents, the direction of liquid flow can be perpendicular and/or tangential to a membrane. Tangential flow is effective for recycling ATP and for preventing membrane plugging and may be superimposed on perpendicular flow. Flow perpendicular to the membrane may be caused or effected by a positive pressure pump or a vacuum suction pump. The solution in contact with the outside surface of the membrane may be cyclically changed, and may be in a steady tangential flow with respect to the membrane. The reactor may be stirred internally or externally by proper agitation means.

During protein synthesis in the reactor, the protein isolating means for selectively isolating the desired protein may include a unit packed with particles coated with antibody molecules or other molecules immobilized with a component for adsorbing the synthesized, desired protein, and a membrane with pores of proper sizes. Preferably, the protein isolating means comprises two columns for alternating use. Alternately, the protein product may be absorbed using expanded bed chromatography, in which case a membrane may or may not be used.

The amount of protein produced in a translation reaction can be measured in various fashions. One method relies on the availability of an assay which measures the activity of the particular protein being translated. An example of an assay for measuring protein activity is a luciferase assay system, or chloramphenical acetyl transferase assay system. These assays measure the amount of functionally active protein produced from the translation reaction. Activity assays will not measure full length protein that is inactive due to improper protein folding or lack of other post translational modifications necessary for protein activity.

Another method of measuring the amount of protein produced in coupled in vitro transcription and translation reactions is to perform the reactions using a known quantity of radiolabeled amino acid such as $^{35}$S-methionine or $^3$H-leucine and subsequently measuring the amount of radiolabeled amino acid incorporated into the newly translated protein. Incorporation assays will measure the amount of radiolabeled amino acids in all proteins produced in an in vitro translation reaction including truncated protein products. The radiolabeled protein may be further separated on a protein gel, and by autoradiography confirmed that the product is the proper size and that secondary protein products have not been produced.

In embodiments using DNA template to drive in vitro transcription/translation, some components of the transcription and/or translation system in the bacterial extract can be advantageously supplemented to increase the availability of such components in the reaction mixture. In a preferred embodiment, the reaction mixture contains one or more of the following: (1) an initial concentration of GTP, UTP and CTP of about 0.5 mM to about 2.0 mM, and preferably about 0.85 mM; (2) an initial concentration of ATP of about 0.5 mM to about 2.5 mM, and preferably about 1.22 mM; (3) an initial concentration of PEP of about 10 mM to about 50 mM, and preferably about 27.0 mM; (4) a concentration of pyruvate kinase of about 0.05 units/ml to about 0.5 units/mL, and preferably about 0.2 units/mL; (5) an initial concentration of tRNAs of about 0.05 mg/mL to about 0.3 mg/mL, and preferably about 0.17 mg/mL; (6) an initial concentration of all 19 amino acids (all amino acids except methionine) of about 0.2 mM to about 0.6 mM, and preferably about 0.35 mM; and (7) an initial concentration of methionine of about 0.6 micromoles/liter ($\mu$M) to about 2.0 mM, and preferably about 4.3 $\mu$M to about 2.0 mM, and more preferably about 0.1 mM to about 2.0 mM, and most preferably about 1.0 mM to about 2.0 mM.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Experimental

Expression of the Serine Protease Domain of Murine Urokinase in a Cell-Free System The standard reaction mixture for cell-free protein synthesis consists of the following components: 57mM Hepes-KOH (pH8.2), 1.2 mM ATP, 0.85 mM each of GTP, UTP and CTP, 0.64 mM cAMP, 200 mM potassium glutamate, 80 mM NH$_4$(OAc), 15 mM Mg(OAc)$_2$, 34 $\mu$g/ml folinic acid, 6.7 $\mu$g/ml plasmid, 33 $\mu$g/ml T7RNA polymerase, 500 $\mu$M each of 20 unlabeled amino acids and ($^3$H) leucine (0.27 GBq/mmol), 2% PEG 8000, 33 mM PEP (phosphoenolpyruvate), 1 mM reduced glutathione(GSH), 4 mM oxidized glutathione (GSSG) and 0.24 volumes of S30 extract. For the expression of serine protease domain of murine urokinase, plasmid pK7UK which contains the coding sequence under the T7 promoter was used.

In certain experiments, *E. coli* dsbC or human PDI protein was added in different concentrations. PDI was purchased from Pierce, Inc. and dsbC was purified from the culture of *E. coli* strain BL21DE3 (pETdsbChisC). T7 RNA polymerase was prepared from the culture of *E. coli* strain BL21(pAR1219) according to the slightly modified procedures of Davanloo et al. (1984) *P.N.A.S.* 81:2035–2039. *E. coli* strain FA113 which carries mutations on trxB and gor was also used.

S30 extract was prepared from *E. coli* K12 (strain A19) according to the procedures reported in Pratt (1984) Coupled Transcription-Translation in Prokaryotic Cell-free Systems, p. 179–209. In Hames, B. D. and Higgins, S. J. (ed.), Transcription and Translation: a Practical Approach. IRL Press, New York. For further treatment of S30 extract, the extract was mixed with 0.1 volume of 20 mM iodoacetamide (IAA) and incubated for 30 minutes at room temperature. To remove the residual IAA or sodium sulfite, the extract was dialyzed against 200 volumes of S30 buffer(10 mM Tris-Cl, pH 7.8, 14 mM Mg(OAc)$_2$, 60 mM K(OAc)) at 4° C. for 4 hours.

For the expression of protein in the semicontinuous system, 210 $\mu$l of standard reaction mixture was incubated in a dialysis chamber (Slide-A-Lyzer, molecular weight cut-off 10,000, Pierce, Ill.) which was placed in 6.0 mL of reservoir buffer (same as the reaction mixture except for the absence of S30 extract, DNA, and T7 RNA polymerase).

All the synthesis reactions were conducted at 37° C. for the given time periods.

Determination of Protein Synthesis Yield. The amount of synthesized protein was estimated from the measured TCA-insoluble radioactivities in a liquid scintillation counter (LS3801, Beckman) as described by Kim, et al. (1996) Eur. J. Biochem. 239: 881–886.

Enzymatic Activity of Cell-Free Synthesized Protease Domain of Urokinase. 20 $\mu$L samples were taken during incubation periods to measure the enzymatic activity of synthesized protein. After centrifuging the samples, 10 mL of supernatant was taken and added to a microplate containing 80 $\mu$L of assay buffer (38 mM NaCl, 50 mM Tris-Cl, pH 8.8) and 10 $\mu$L of substrate solution (2 mM Chromozyme U, Roche Molecular Biochemicals, CA). The change in absorbance at 405 nm was measured in a microplate reader (SpectraMax 190, Molecular Devices, CA).

Analysis of Reduced Glutathione Concentration. The concentration of reduced glutathione was measured using dithionitrobenzoic acid (DTNB). A 4.0 mg/mL DTNB solution was prepared in 1M Tris-Cl solution (pH 7.8). 10 μL samples were mixed with the same volume of 10% TCA to stop the enzymatic reduction and centrifuged. To determine the concentration of reduced glutathione, 10μL of supernatant and 10μL of DTNB solution were added to 80μL of I M Tris-Cl solution in a microplate. After 3 minutes, absorbances at 412 nm were measured and the concentration of glutathione was determined from a standard curve.

Construction of mutant strains. Insertional mutations in trxB or gor in the strain FA113 (Bessette et al. (1999) P.N.A.S. 96(24):13703–8) were moved into strain A19 by P1 transduction following the standard procedures (Miller (1992) A Short Course in Bacterial Genetics. p. 263–364. Cold Spring Harbor Press, N.Y.)

Results

Figure 2:
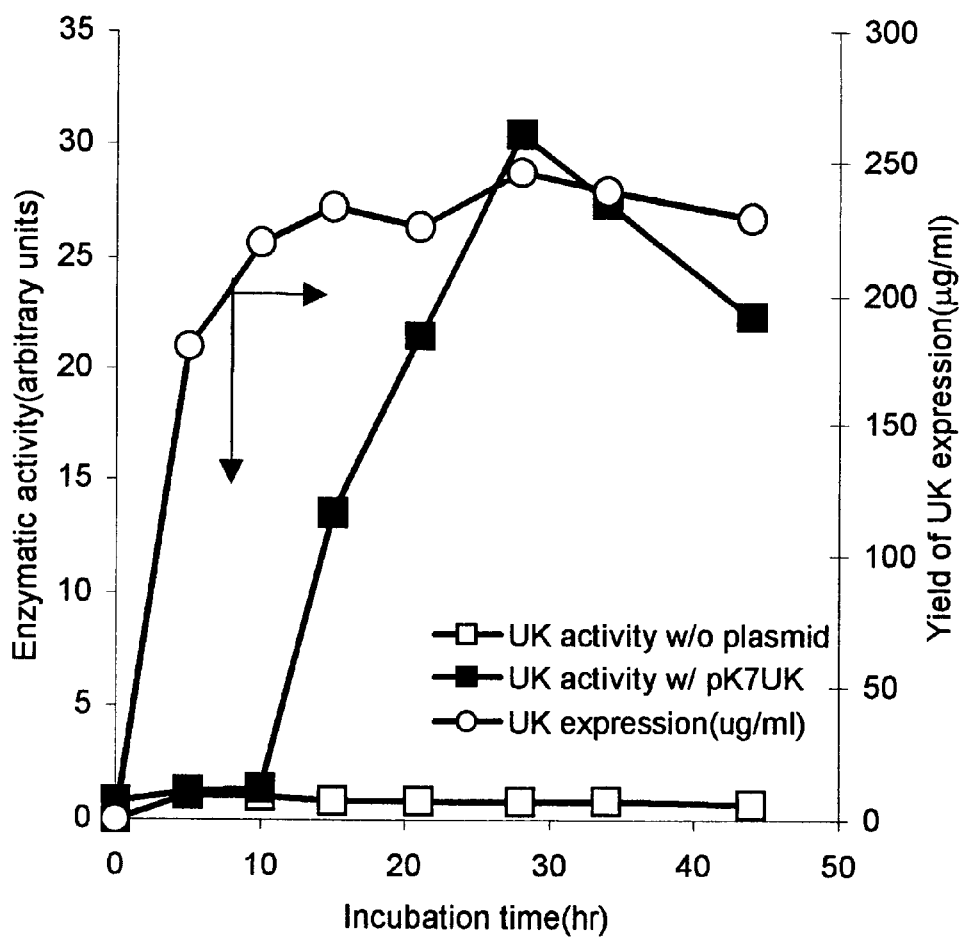
FIG. 2 is a graph depicting the synthesis of urokinase and its enzymatic activity during a semi-continuous reaction.

210 μL of reaction mixture was prepared and incubated in the semi-continuous reactor depicted in FIG. 1. 10 μL samples were withdrawn during the incubation to determine the amount of synthesized protein (shown in FIG. 2, open circles). At the same time, 20 μL samples were taken for the measurement of serine protease activity (open squares, reaction without plasmid; filled squares, reaction with the plasmid pK7UK).

Figure 3:
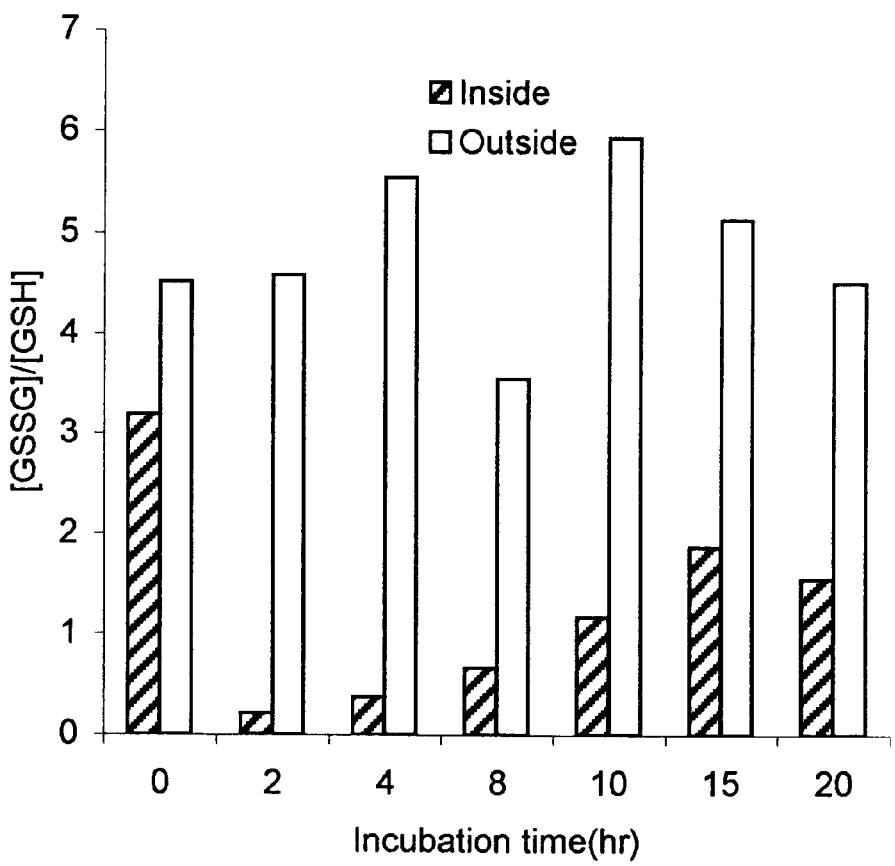
FIG. 3 is a bar graph depicting the change in redox potential during semi-continuous synthesis.

To monitor the change in redox potential, 10 μL samples were taken from the reaction mixture and reservoir solution. The concentrations of reduced glutathione were measured as described in materials and methods. Concentrations of oxidized glutathione were estimated based on the initial concentrations and the measured amounts of reduced glutathione. The results are shown in FIG. 3. The initial concentrations of reduced and oxidized glutathione were 1 mM and 4 mM, respectively.

Figure 4:
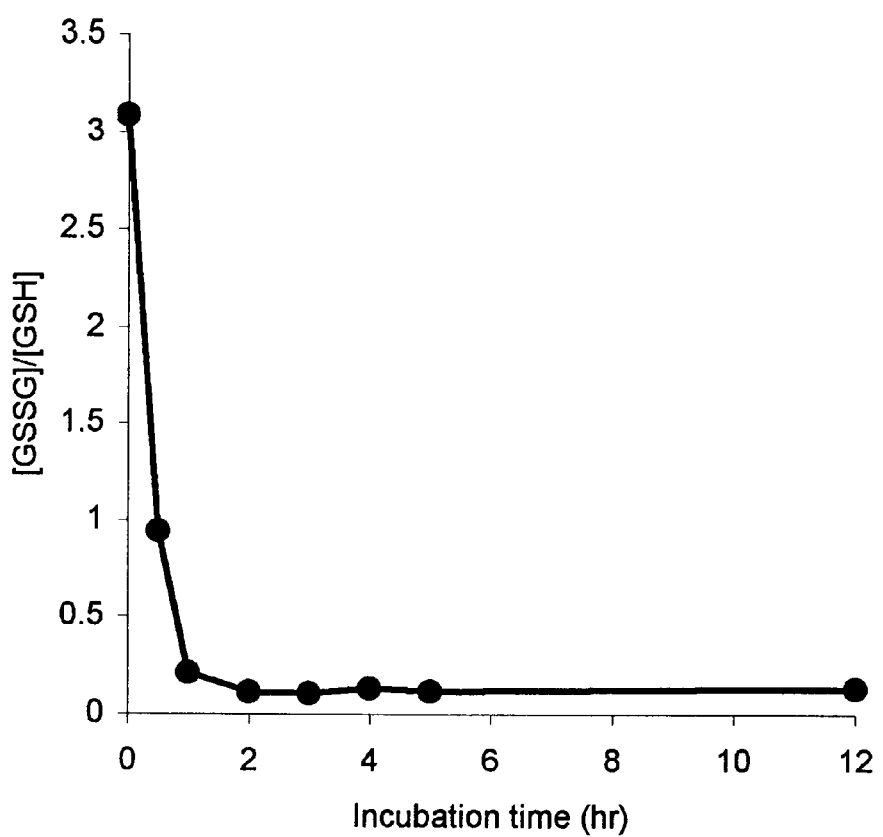
FIG. 4 is a time course showing the reduction of glutathione in a batch synthesis reaction.

To monitor the time course of reduced glutathione in a batch reaction, during the incubation of a 150 μL batch reaction, 10 μL samples were taken at the given time points, treated with TCA solution, and the concentrations determined. The concentrations of reduced glutathione were measured as described in materials and methods. Concentrations of oxidized glutathione were estimated based on the initial concentrations and the measured amounts of reduced glutathione. The results are shown in FIG. 4. The initial concentrations of reduced and oxidized glutathione were 1 mM and 4 mM respectively.

Figure 5:
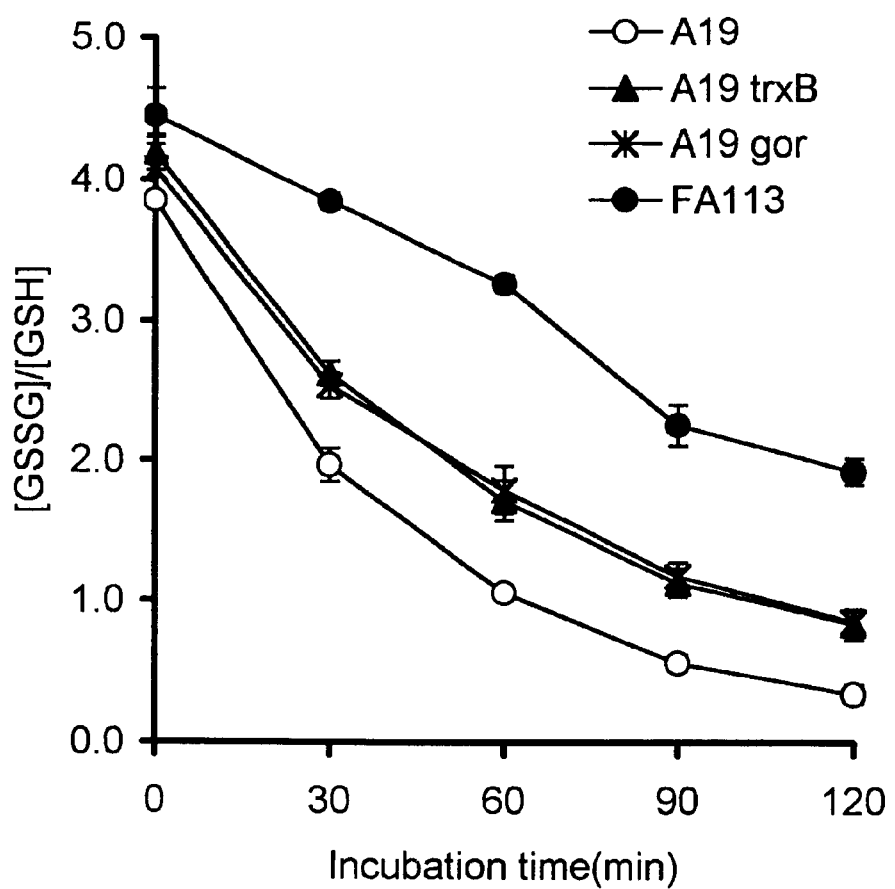
FIG. 5 shows the reduction of glutathione in the presence of extracts from different bacterial strains.

To determine the effects of different strains on glutathione reduction, cell extracts were prepared from the mutant strains indicated in FIG. 5, and were incubated with the reaction mix. 10 μL samples were taken at the given time points, treated with TCA solution and the concentrations of GSH determined as described above. Cell extracts were prepared by brief sonication of cell paste resuspended in S30 buffer. Total concentrations of cellular proteins in the reaction mixtures were 6.8 (A19); 5.2 (A19 trxB); 5.5 (A19 gor); and 5.4 (FA113) mg/mL, respectively. In experiments with the A19 cell extract used for protein synthesis the concentration of cellular protein was 10.8 mg/mL.

Figure 6:
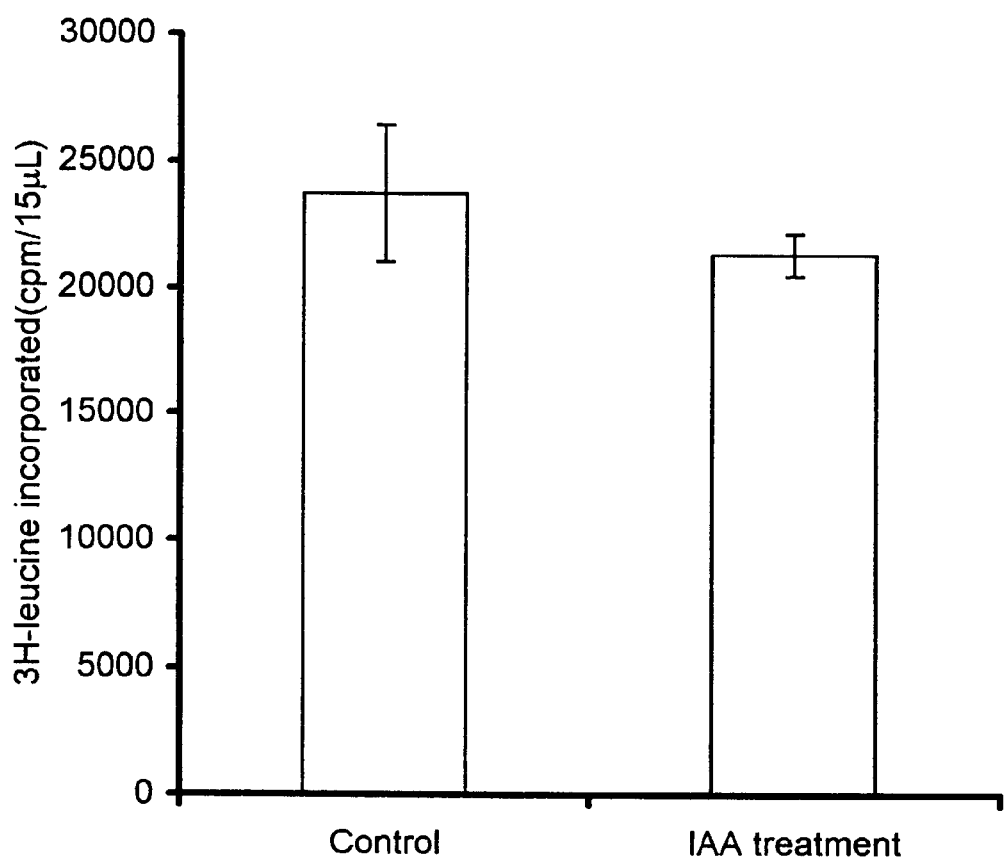
FIG. 6 is a bar graph depicting the expression of urokinase in control and IAA treated extracts.

The expression of urokinase was determined from the IAA-treated extract, as shown in FIG. 6. Plasmid pK7UK was treated in the standard reaction mixtures containing normal or IAA treated cell extract. After a 1 hour incubation, amounts of TCA-insoluble radioactivities were measured as described in the experimental methods.

Figure 7A:
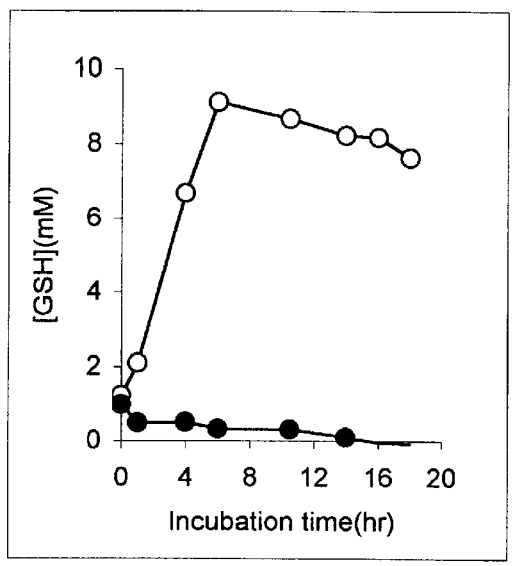
FIGS. 7A and 7B show time courses of glutathione reduction and enzymatic activity of product in control and IAA treated extracts.
Figure 7B:
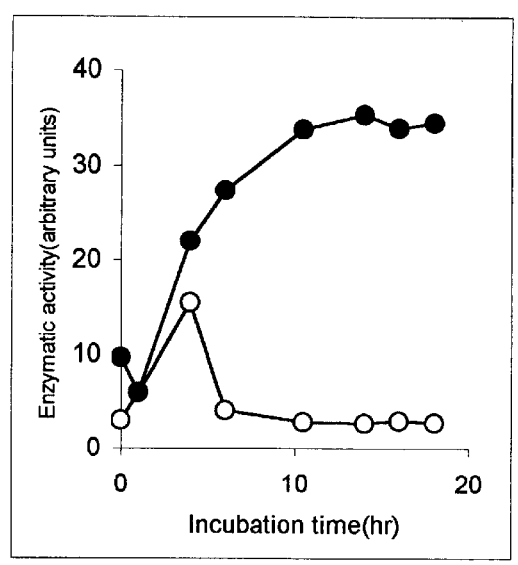

Time courses of glutathione reduction and enzymatic activity of the expressed protein in a batch reaction are shown in FIG. 7. Plasmid pK7UK was expressed in a 450 μL reaction mixture containing either untreated or IAA treated S30 extract and 5mM glutathione buffer (1mM reduced form and 4mM oxidized form). At the given time points, 40 μL samples were withdrawn and assayed for GSH concentration (panel A) and enzymatic activity(panel B) as described in the Materials and Methods. Open circles, reaction with normal cell-extract; closed circles, reaction with IAA treated cell-extract.

Figure 8:
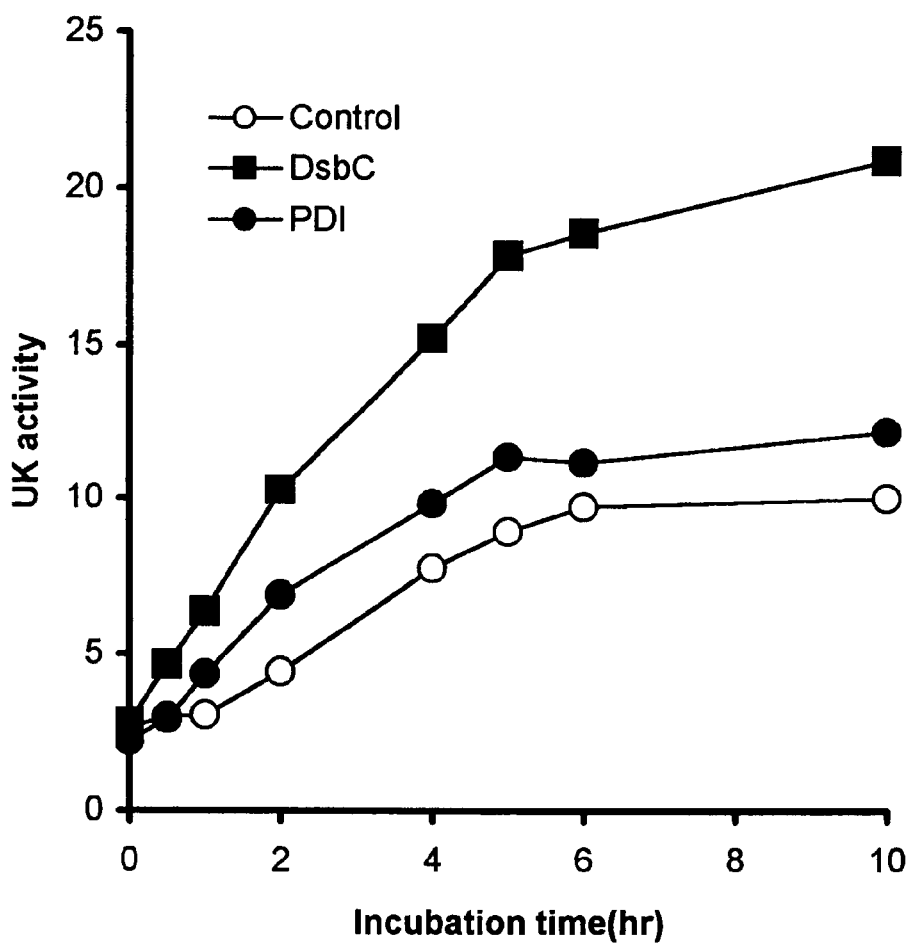
FIG. 8 is a time course of the synthesis of urokinase in the presence of PDI or dsbC.

In FIG. 8, the effect of PDI or dsbC on the rate of active protein syntheis is shown. To a reaction with IAA treated cell extract, 133 μg/mL dsbC or 27 μg/mL of PDI was added. 20 μL samples were taken during the incubation and the enzymatic activities were measured as described. Open circles (control reaction without foldase); closed circles (addition of PDI); closed squares (addition of DsbC).

What is claimed is:

1. A method for in vitro synthesis of polypeptides comprising at least one disulfide bond, in a reaction mix comprising a biological extract comprising components of polypeptide synthesis machinery, wherein such components are capable of expressing a nucleic acid encoding a desired polypeptide, the improvement comprising:
    synthesizing said polypeptide in a reaction mix wherein said biological extract has been pre-treated with a sulfhydryl inactivating agent that alkylates or acetylated free sulfhydryl groups;
    isolating said polypeptide from said reaction mixture, wherein the amount of said polypeptide that is properly folded is enhanced relative to polypeptide synthesized in the absence of pretreatment with said sulfhydryl inactivating agent.

2. The method according to claim 1, wherein said sulfhydryl inactivating agent is selected from the group consisting of iodoacetamide, N-ethyl maleimide, iodoacetate, and N-iodoacetyl-N'-(5-sulfonic-1-naphthyl) ethylene diamine.

3. The method according to claim 2, wherein said sulfhydryl inactivating agent is iodoacetamide.

4. A method for in vitro synthesis of polypeptides comprising at least one disulfide bond in a reaction mix comprising a biological extract comprising components of polypeptide synthesis machinery, wherein such components are capable of expressing a nucleic acid encoding a desired polypeptide, the improvement comprising:
    synthesizing said polypeptide in a reaction mix wherein said biological extract has been pre-treated with a sulfhydryl inactivating agent that alkylates or acetylated free sulfhydryl groups, wherein said reaction mix further comprises a redox buffer;
    isolating said polypeptide from said reaction mixture, wherein the amount of said polypeptide that is properly folded is enhanced relative to polypeptide synthesized in the absence of pretreatment with said sulfhydryl inactivating agent.

5. The method according to claim 4, wherein said redox buffer is selected from the group consisting of glutathione, dithiothreitol, dithioerythritol, β-mercaptoethanol, thioglycolate and cysteine.

6. The method according to claim 5, wherein said redox buffer comprises a glutathione at a concentration of at least 1 mM and not more than 25 mM in a mixture of oxidized and reduced form.

7. The method according to claim 6, wherein said mixture is a ratio of 4:1 oxidized to reduced.

8. The method according to claim 1, wherein said biological extract is a bacterial cell extract from a bacterial cell that has been genetically modified to inactivate at least one of thioredoxin reductase and glutathione reductase.

9. A method for in vitro synthesis of polypeptides comprising at least one disulfide bond in a reaction mix comprising a biological extract comprising components of polypeptide synthesis machinery, wherein such components are capable of expressing a nucleic acid encoding a desired polypeptide, wherein such components are capable of expressing a nucleic acid encoding a desired polypeptide, the improvement comprising:

synthesizing said polypeptide in a reaction mix comprising a redox buffer, wherein said biological extract has been pre-treated with a sulfhydryl inactivating agent that alkylates or acetylated free sulfhydryl groups, wherein said reaction mixture comprises a foldase enzyme;

isolating said polypeptide from said reaction mixture, wherein the amount of said polypeptide that is properly folded is enhanced relative to polypeptide synthesized in the absence of pretreatment with said sulfhydryl inactivating agent.

10. The method according to claim 9, wherein said foldase enzyme is selected from the group consisting of DsbA, DsbB, DsbC, DsbD, PDI (protein disulfide isomerase), GroEL/ES, DnaK, DnaJ, GrpE, BIP (immunoplobulin heavy chain binding protein), PPI (peptidylprolyl isomerase) and cyclophilin.

11. The method according to claim 10, wherein said foldase is DsbC.

12. The method according to claim 10, wherein said foldase is PDI.

\* \* \* \* \*